(12) United States Patent
Peckham

(10) Patent No.: US 8,014,849 B2
(45) Date of Patent: Sep. 6, 2011

(54) ROTATIONAL MARKERS

(75) Inventor: John Eric Peckham, Sunnyvale, CA (US)

(73) Assignees: Stryker Corporation, Kalamazoo, MI (US); Stryker NV Operations Limited, Dublin (IE)

(*) Notice: Subject to any disclaimer, the term of this patent is extended or adjusted under 35 U.S.C. 154(b) by 1627 days.

(21) Appl. No.: 10/719,421

(22) Filed: Nov. 21, 2003

(65) Prior Publication Data

US 2005/0113686 A1    May 26, 2005

(51) Int. Cl.
    *A61B 19/00* (2006.01)
(52) U.S. Cl. ...................................................... 600/424
(58) Field of Classification Search .................. 600/424, 600/414, 407
    See application file for complete search history.

(56) References Cited

U.S. PATENT DOCUMENTS

| | | | |
|---|---|---|---|
| 4,693,237 A * | 9/1987 | Hoffman et al. | 128/899 |
| 4,718,417 A * | 1/1988 | Kittrell et al. | 606/7 |
| 5,047,050 A | 9/1991 | Arpesani | 623/1 |
| 5,091,205 A | 2/1992 | Fan | 427/2 |
| 5,203,777 A * | 4/1993 | Lee | 604/529 |
| 5,425,709 A * | 6/1995 | Gambale | 604/103.05 |
| 5,489,277 A * | 2/1996 | Tolkoff et al. | 604/529 |
| 5,607,442 A | 3/1997 | Fischell et al. | 606/191 |
| 5,681,336 A * | 10/1997 | Clement et al. | 606/159 |
| 5,741,327 A * | 4/1998 | Frantzen | 623/1.34 |
| 5,755,770 A | 5/1998 | Ravenscroft | 623/1 |
| 5,824,042 A * | 10/1998 | Lombardi et al. | 623/1.13 |
| 5,824,046 A | 10/1998 | Smith et al. | 623/1 |
| 5,921,978 A * | 7/1999 | Thompson et al. | 604/529 |
| 6,083,167 A * | 7/2000 | Fox et al. | 600/439 |
| 6,159,165 A | 12/2000 | Ferrera et al. | 600/585 |
| 6,165,194 A * | 12/2000 | Denardo | 606/191 |
| 6,174,330 B1 | 1/2001 | Stinson | 623/1.34 |
| 6,179,851 B1 | 1/2001 | Barbut et al. | 606/159 |
| 6,251,135 B1 | 6/2001 | Stinson et al. | 623/1.34 |
| 6,264,671 B1 * | 7/2001 | Stack et al. | 606/198 |
| 6,270,509 B1 | 8/2001 | Barry et al. | 606/159 |
| 6,285,903 B1 | 9/2001 | Rosenthal et al. | 600/433 |
| 6,293,966 B1 | 9/2001 | Frantzen | 623/1.15 |
| 6,302,875 B1 * | 10/2001 | Makower et al. | 604/528 |
| 6,315,790 B1 | 11/2001 | Gerberding et al. | 623/1.11 |
| 6,340,367 B1 * | 1/2002 | Stinson et al. | 623/1.34 |

(Continued)

FOREIGN PATENT DOCUMENTS

DE    103 17 241 A1    10/2004

(Continued)

OTHER PUBLICATIONS

U.S. Appl. No. 10/600,022, filed Jun. 19, 2003, Brent Gerberding, Bhavesh Mistry.

*Primary Examiner* — Tse Chen
*Assistant Examiner* — Jacqueline Cheng
(74) *Attorney, Agent, or Firm* — Vista IP Law Group LLP

(57) ABSTRACT

A medical device includes a rotational marker. A marker may be viewable under an imaging device, such as a fluoroscope or an MRI system. A rotational marker allows the rotational orientation of a medical device to be determined with respect to the surrounding environment. A medical device including a rotational marker may comprise an implantable medical device, a delivery system for delivery of an implantable medical device, and the like.

24 Claims, 27 Drawing Sheets

U.S. PATENT DOCUMENTS

| | | | |
|---|---|---|---|
| 6,361,759 B1 | 3/2002 | Frayne et al. | 424/9.323 |
| 6,395,018 B1 | 5/2002 | Castaneda | 623/1.13 |
| 6,416,490 B1 * | 7/2002 | Ellis et al. | 604/22 |
| 6,497,711 B1 * | 12/2002 | Plaia et al. | 606/159 |
| 6,503,261 B1 | 1/2003 | Bruneau et al. | 606/159 |
| 6,569,005 B2 | 5/2003 | Maxwell | 452/128 |
| 6,574,497 B1 * | 6/2003 | Pacetti | 600/420 |
| 6,576,009 B2 * | 6/2003 | Ryan et al. | 623/1.35 |
| 6,579,311 B1 * | 6/2003 | Makower | 623/1.23 |
| 6,660,024 B1 * | 12/2003 | Flaherty et al. | 600/439 |
| 6,685,648 B2 * | 2/2004 | Flaherty et al. | 600/464 |
| 6,726,677 B1 * | 4/2004 | Flaherty et al. | 604/528 |
| 6,957,098 B1 * | 10/2005 | Hyde et al. | 600/424 |
| 7,153,277 B2 * | 12/2006 | Skujins et al. | 600/585 |
| 2002/0032432 A1 * | 3/2002 | Nash et al. | 604/533 |
| 2002/0099431 A1 * | 7/2002 | Armstrong et al. | 623/1.11 |
| 2003/0167052 A1 * | 9/2003 | Lee et al. | 604/529 |
| 2003/0195614 A1 | 10/2003 | Ryan et al. | 623/1.16 |

FOREIGN PATENT DOCUMENTS

EP          1 166 721 A2    10/1996

* cited by examiner

ROTATIONAL MARKERS

BACKGROUND OF THE INVENTION

Implantable medical devices, such as a stents, grafts, stent-grafts, vena cava filters and the like, and delivery assemblies for implantable medical devices are utilized in a number of medical procedures and situations, and as such their structure and function are generally known in the art.

A stent is an elongated device used to support an intraluminal wall. In the case of stenosis, a stent provides a conduit for blood in the area of the stenosis. Such a stent may also have a prosthetic graft layer of fabric or other covering lining the inside or outside thereof, such a covered stent being commonly referred to in the art as an intraluminal prosthesis, an endoluminal or endovascular graft (EVG), or a stent-graft.

A stent-graft may be used, for example, to treat a vascular aneurysm by removing the pressure on a weakened part of an artery so as to reduce the risk of rupture. Typically, a stent-graft is implanted in a blood vessel at the site of a stenosis or aneurysm endoluminally, i.e. by so-called "minimally invasive techniques" in which the stent-graft, restrained in a radially compressed configuration by a sheath or catheter, is delivered by a deployment system or "introducer" to the site where it is required. The introducer may enter the body through the patient's skin, or by a "cut down" technique in which the entry blood vessel is exposed by minor surgical means. When the introducer has been threaded into the body lumen to the prosthesis deployment location, the introducer is manipulated to cause the stent-graft to be ejected from the surrounding sheath or catheter in which it is restrained (or alternatively the surrounding sheath or catheter is retracted from the prosthesis), whereupon the stent-graft expands to a predetermined diameter at the deployment location, and the introducer is withdrawn. Stent expansion may be effected by a variety of mechanisms, including spring elasticity, balloon expansion, or by the self-expansion of a thermally or stress-induced return of a memory material to a pre-conditioned expanded configuration.

A stent-graft may include only a partial covering. Partially covered stent-grafts are particularly useful at a vessel branch or bifurcation, where the device may be positioned to cover an aneurism without an adverse consequential blocking of an opposing side branch vessel. Therefore, a partially covered stent-graft must be placed having a specific rotational orientation with respect to the surrounding environment.

There remains a need for a device which allows for proper rotational orientation of implantable medical devices within a bodily lumen.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In one embodiment, the invention is directed to an apparatus comprising a medical device and a marker wire coupled to the medical device. The marker wire may extend such that a first portion of the marker wire extends in a circumferential direction about the longitudinal axis of the medical device and a second portion of the marker wire extends in a direction parallel to the longitudinal axis of the medical device. Desirably, the rotational orientation of the marker wire can be determined using an imaging device when the medical device is positioned within a bodily lumen.

In another embodiment, the invention is directed to a medical device including a first marker coupled to the medical device and a second marker coupled to the medical device, wherein the first marker appears more visible than the second marker when viewed through an imaging device. In some embodiments, the first marker may comprise a marker strip running parallel to the longitudinal axis of the medical device and the second marker may comprise a marker strip running parallel to the longitudinal axis of the medical device.

In another embodiment, the invention is directed to a medical device including a marker wire. The marker wire may have a first end and a second end, the first end and the second end being offset from one another along the length of the device. The first end and the second end may further be offset from one another in a circumferential direction about the longitudinal axis of the device. Desirably, the rotational orientation of the marker wire may be determined using an imaging device when the medical device is positioned within a bodily lumen.

An inventive medical device may further include a port, and may include a rotational ablation device or be used in conjunction with a rotational ablation device to remove deposits from a vessel wall.

The invention is also directed to a method of using any of the inventive devices disclosed herein for determining the rotational orientation of a device within a bodily lumen.

In another embodiment, the invention is directed to a method of positioning an implantable medical device within a bodily lumen. An inventive medical device having a rotational marker may be provided, inserted into a bodily lumen and maneuvered to a deployment site. The deployment site and the device may then be viewed through an imaging device, the rotational marker being visible upon the imaging device. The medical device may then be positioned to a proper rotational orientation using the rotational marker as viewed upon the imaging system.

A rotational marker or rotational marker system may comprise any of the inventive concepts disclosed herein that allow the rotational orientation of a medical device to be determined when viewed upon an imaging device.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
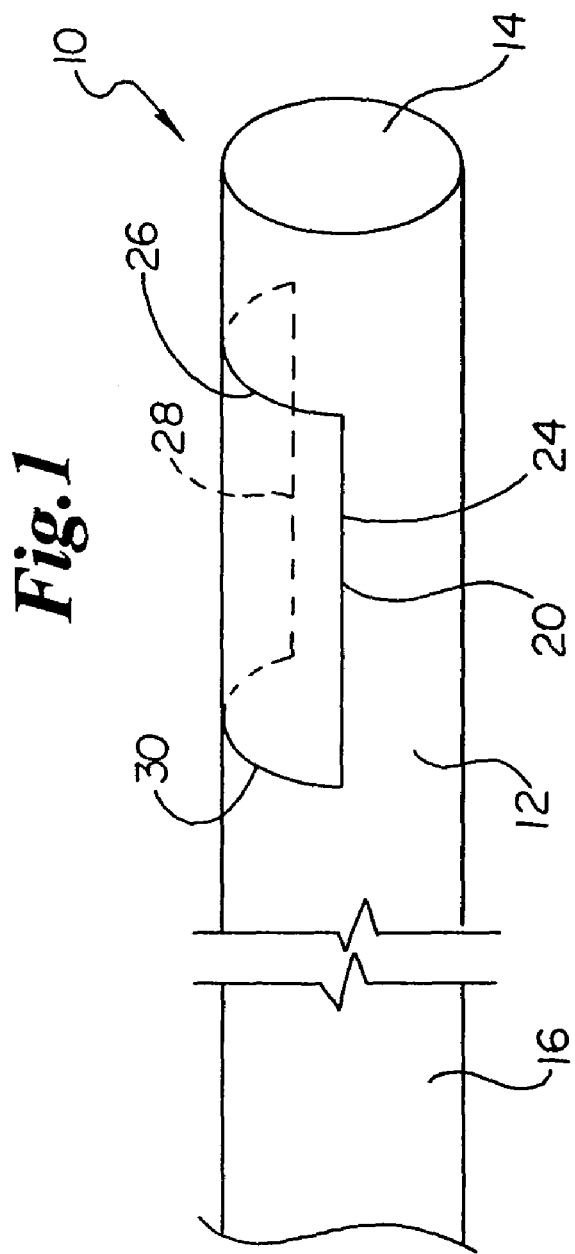
FIG. 1 is a perspective view of an embodiment of an inventive medical device having a rotational marker.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

The present inventive device allows for proper rotational orientation of an implantable medical device, such as a stent, stent-graft, vena cava filter, distal protection device, or the like. The inventive device may also allow for proper rotational orientation of a delivery device, such as a catheter.

FIG. 1 shows a medical device 10 having a rotational marker 20. Desirably, the rotational marker 20 is arranged to allow for a determination of the rotational orientation of the medical device 10 with respect to the surrounding environment. A rotational marker 20 may be mounted to the surface of a medical device 10 or may be partially or fully recessed beneath the surface.

The rotational marker 20 is desirably viewable after insertion into a bodily lumen through an imaging device such as a fluoroscope or an MRI system. Markers 20 may comprise radiopaque markers. Markers 20 may comprise MRI markers.

Radiopaque markers 20 may be any suitable radiopaque material, such as barium, bismuth, tungsten, gold, titanium, iridium, platinum, palladium, silver, rhenium, tantalum, niobium, molybdenum, rhodium, palladium, hafnium, iridium or alloys or composites of these materials, and others, such as disclosed in U.S. Pat. No. 6,315,790, incorporated herein by reference.

MRI markers 20 may be any suitable material, and desirably a ferro-magnetic, superparamagnetic or paramagnetic material, such as gadolinium, iron or manganese containing alloys, or gadolinium-DTPA (diethylene triamine pentaacetic acid) chelates as disclosed in U.S. Pat. No. 6,361,759, incorporated herein by reference.

Markers 20 may comprise a single composition of material. Markers 20 may also have a plurality of sections or portions of differing materials. Various materials may be more or less visible when viewed through an imaging device. Thus, certain portions of a rotational marker 20 may be more or less visible than other portions of the marker 20.

Rotational markers 20 may be attached to the medical device 10 using any suitable method. For example, markers 20 may be bonded to the device 10 with an adhesive. Markers 20 may be attached to the device 10 using RF energy, IR energy, UV energy, laser energy, ultra-sonic energy, electrical energy, and any combination thereof. The application of energy may physically bond the material of the marker 20 with the material of the device 10. In some embodiments, the application of energy may melt only the material of the device 10, allowing the material of the device 10 to surround the marker 20. Markers 20 may also be inserted into the device 10 as the device is being formed, such as during extrusion or molding of the device 10.

In one embodiment, as shown in FIG. 1, the medical device 10 may comprise a catheter shaft 12 having a distal end 14 and a proximal end 16. Generally, an implantable medical device may be disposed about the catheter shaft 12 for delivery into a bodily lumen.

A catheter 12 may be made from any suitable material, such as polyesters and copolymers thereof such as those sold including polyalkylene terephthalates such as polyethylene terephthalate (PET) and polybutylene terephthalate (PBT) available under the tradename of EKTAR® available from Eastman Chemical Co. in Kingsport, Tenn., polycyclohexylene terephthalate (PCT); poly(trimethylene terephthalate) (PTT), PCTG and poly(cyclohexanedimethanol-co-ethylene terephthalate) (PETG) copolyesters available under the tradename of EASTAR® available from Eastman Chemical Co., PCTA available under the tradename of DURASTAR® available from Eastman Chemical Co., poly(ethylene naphthalate) (PEN) polyester available from DuPont in Wilmington, Del. under the tradename of TEONEX®; and so forth; polyester elastomers (PEELs); polyamides such as amorphous nylon and nylon 12 such as those available from Elf Atochem under the tradename of CRISTAMID® and copolymers thereof such as GRILAMID® TR-55-LX nylon 12 polyether-block-amide available from EMS-American Grilon in Sumter, S.C.; polyetherimides available from GE Plastics under the tradename of ULTEM®; polystyrene and expandable polystyrene (EPS); acrylonitrile-butadiene-styrene (ABS); styrene-acrylonitrile (SANs); polyphenylene sulfide (PPS); polyphenylene oxides (PPO); interpolymers of PPO and EPS; polyetherketones (PEEK); polyolefins such as polyethylenes and polypropylenes including low, medium and high densities such as HDPE available under the tradename of ALATHON® from Equistar Chemicals; amorphous polyolefins; polyether-block-amides such as those sold under the tradename of PEBAX® available from Elf Atochem; polyimides; polyurethanes; polycarbonates; polyethers; silicones; as well as any copolymers thereof. The above list is intended for illustrative purposes only, and is not intended to limit the scope of the present invention. One of ordinary skill in the art has knowledge of such polymeric materials.

In some embodiments, a rotational marker 20 may comprise a wire. A wire marker 20 may be a generally elongate element having any desired shape and may contain portions having a straight, arcuate, sinuous or serpentine longitudinal axis. Further, a wire marker 20 may have any cross-sectional shape.

As shown in FIG. 1, a wire marker 20 may comprise a first portion 24 extending along a portion of the length of the medical device 10, and a second portion 26 extending about a radial arc or circumferential portion of the medical device 10. The marker 20 may further include a third portion 28 extending along a portion of the length of the medical device 10, and a fourth portion 30 extending about a radial arc or circumferential portion of the medical device 10. The first portion 24 and the third portion 28 may comprise generally lengthwise portions and may be parallel to one another and have the same length. In some embodiments, first portion 24 and the third portion 28 may be parallel to the longitudinal axis of the medical device 10. The second portion 26 and the fourth portion 30 may comprise generally arcuate portions, may be parallel to one another and may have the same arcuate length. In some embodiments, a wire marker 20 may comprise only a lengthwise portion 24. In some embodiments, a wire marker 20 may comprise only an arcuate portion 26.

Arcuate portions 26, 30 may also be characterized as extending in a circumferential direction about the longitudinal axis of the medical device 10. A portion that extends in a circumferential direction about the longitudinal axis of the medical device 10 may be contained within a plane perpendicular to the longitudinal axis of the medical device 10. However, such a portion is not required to be located a constant radial distance from the longitudinal axis of the medical device 10. Thus, radial distance from the longitudinal axis of the medical device 10 as the arcuate portion 26, 30 is traversed may be variable.

A rotational marker 20 comprising a wire may be continuous along its length. Further, the wire marker 20 may include a closed circuit, wherein each section 24, 26, 28, 30 is coupled at one end to an adjacent section 24, 26, 28, 30 and at the other end to another adjacent section 24, 26, 28, 30.

Figure 2:
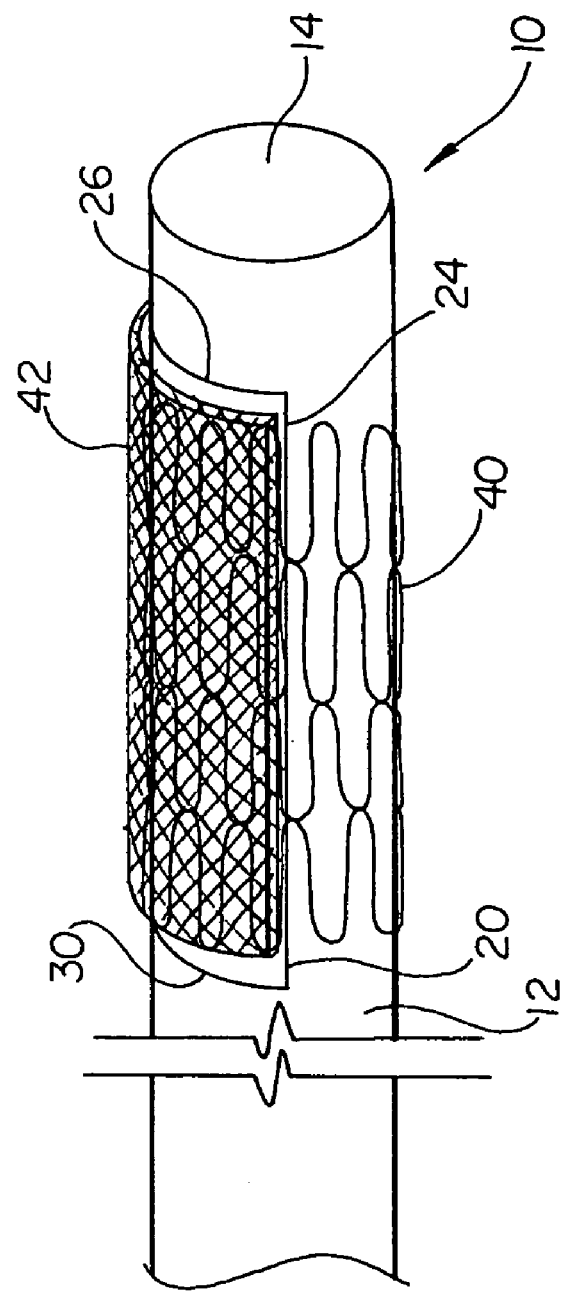
FIG. 2 is a perspective view of an embodiment of an inventive medical device having a rotational marker and a stent-graft.

FIG. 2 shows a medical device 10 comprising a catheter 12 having a rotational marker 20, and an implantable medical device 40, such as a stent or stent-graft, mounted upon the catheter 12. A stent 40 may include a graft portion 42 or other covering over a portion of the stent 40. Suitable coverings include nylon, collagen, PTFE and expanded PTFE, polyethylene terephthalate and KEVLAR, or any of the materials disclosed in U.S. Pat. Nos. 5,824,046 and 5,755,770. More generally, any known graft material may be used including synthetic polymers such as polyethylene, polypropylene, polyurethane, polyglycolic acid, polyesters, polyamides, their mixtures, blends and copolymers. Desirably, the graft portion 42 is located in relation to the rotational marker 20 such that the rotational marker 20 can be used to correctly position the graft 42 within a bodily lumen.

The size and location of rotational markers 20 on a medical device 10 may be adjusted as suitable for the particular application. For example, lengthwise portions 24, 28 of the marker 20 may be substantially coextensive with an implantable medical device 40, or may extend slightly beyond the ends of an implantable medical device 40. Further, lengthwise portions 24, 28 may be placed near the edges of a graft portion 42. Arcuate portions 26, 30 may have an arc length similar to the arc length of a graft portion 42. Thus, if a graft portion extends 180° about the circumference of the stent 40, the arcuate portions 26, 30 may have an arc length of 180°.

Lengthwise portions 24, 28 may be of any suitable length. For example, the length of a lengthwise portion 24, 28 could range from 0.1 millimeter to over 1 meter. Desirably, the length of a lengthwise portion 24, 28 will range from 5 millimeters to 130 millimeters.

Arcuate portions 26, 30 may also be of any suitable arc length, such as ranging from 0.1° to a full 360°. Desirably, arcuate portions 26, 30 have an arc length ranging from 90° to 180°.

It is within the purview of the invention to utilize dimensions that do not correspond to a predetermined implantable medical device 40. For example, length of a rotational marker 20 may be longer or shorter than the length of an implantable medical device 40. The arc length of appropriate portions of a rotational marker 20 may be more or less than the arc length of a graft portion 42. When dimensions of a rotational marker 20 vary from the dimensions of an implantable medical device 40, it may be desirable to align the midpoints of portions of the marker 20 with the midpoints of portions of the implantable medical device 40. For example, the lengthwise midpoint of a stent 40 may be positioned near the midpoint of a lengthwise portion 24, 28 of a rotational marker 20. Similarly, the midpoint of arcuate portions 26, 30 of a rotational marker 20 may be positioned near the midpoint of a graft portion 42 about the circumference of the stent 40.

Figure 3A:
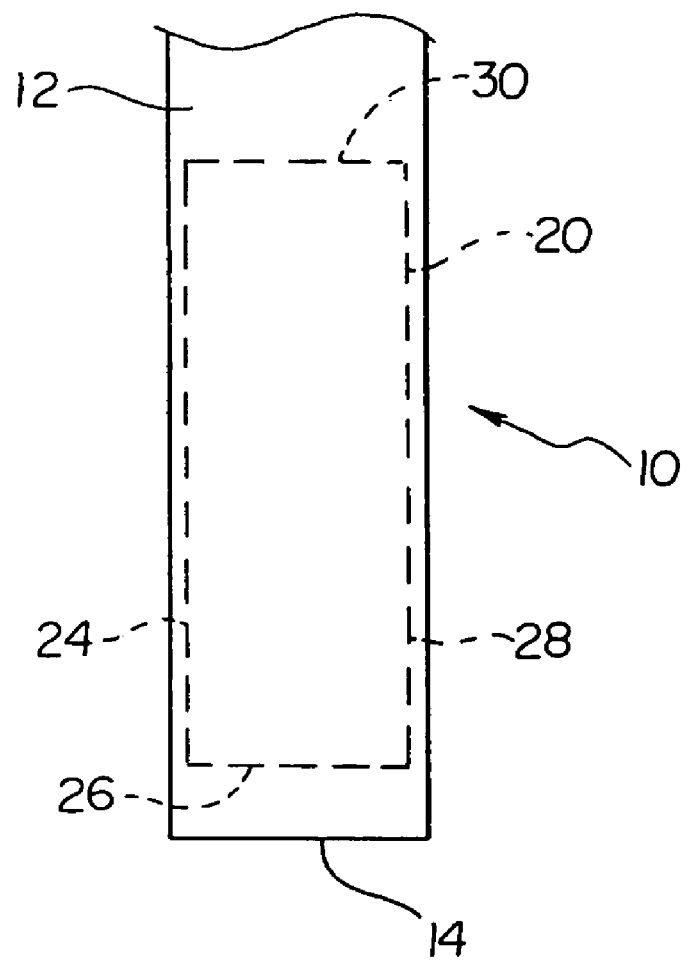
FIG. 3A is a top plan view of an embodiment of an inventive medical device having a rotational marker at a first rotational orientation.
Figure 3B:
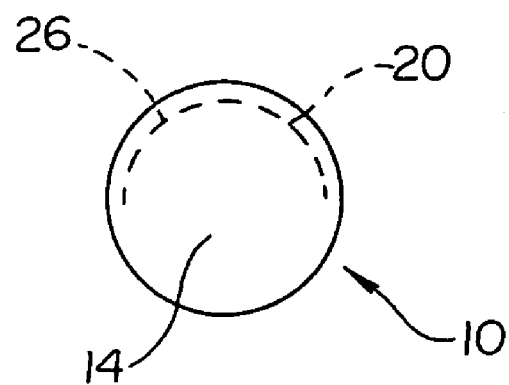
FIG. 3B is an end view of an embodiment of an inventive medical device having a rotational marker at a first rotational orientation.
Figure 3C:
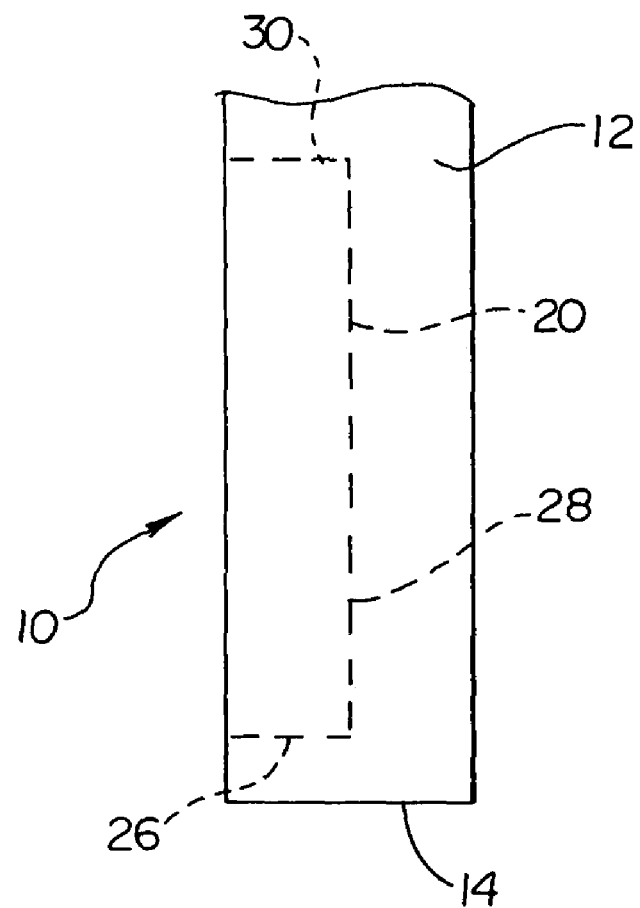
FIG. 3C is a top plan view of an embodiment of an inventive medical device having a rotational marker at a second rotational orientation.
Figure 3D:
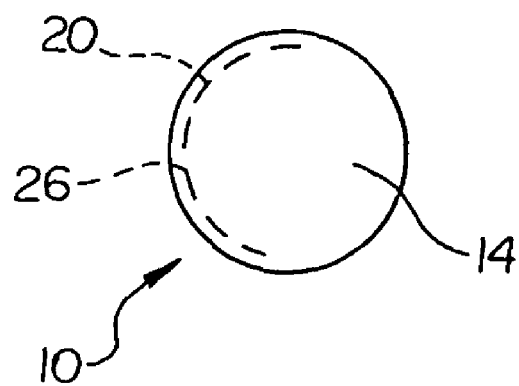
FIG. 3D is an end view of an embodiment of an inventive medical device having a rotational marker at a second rotational orientation.
Figure 3E:
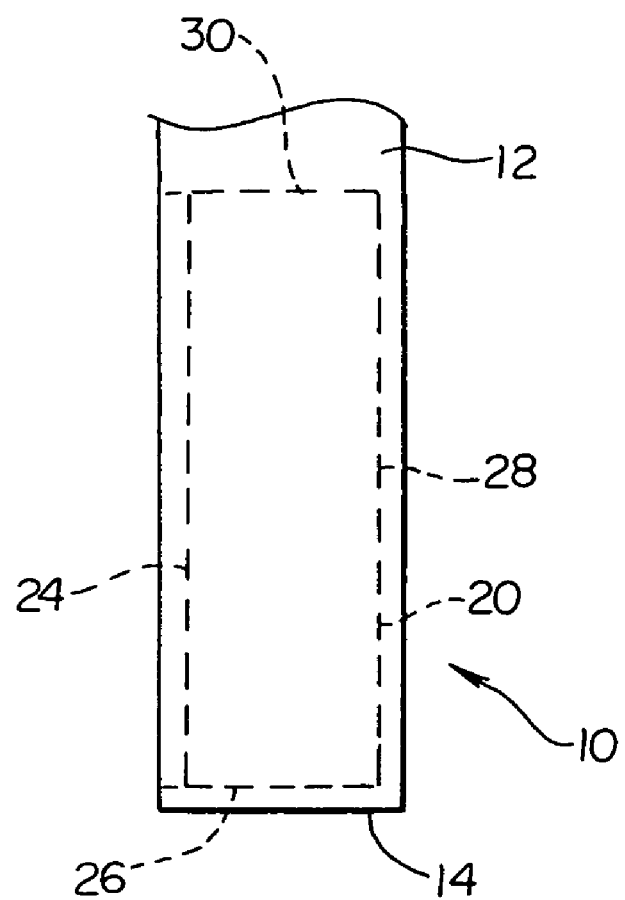
FIG. 3E is a top plan view of an embodiment of an inventive medical device having a rotational marker at a third rotational orientation.
Figure 3F:
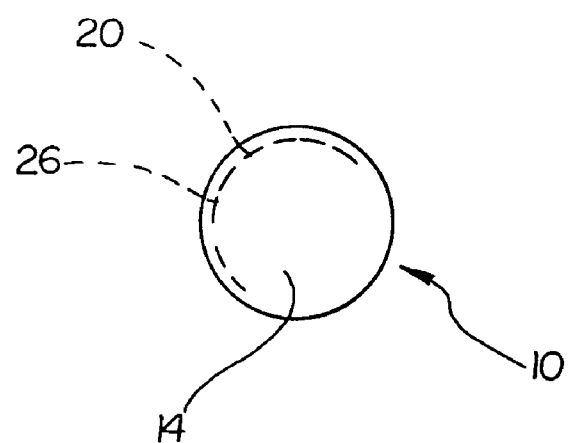
FIG. 3F is an end view of an embodiment of an inventive medical device having a rotational marker at a third rotational orientation.
Figure 3G:
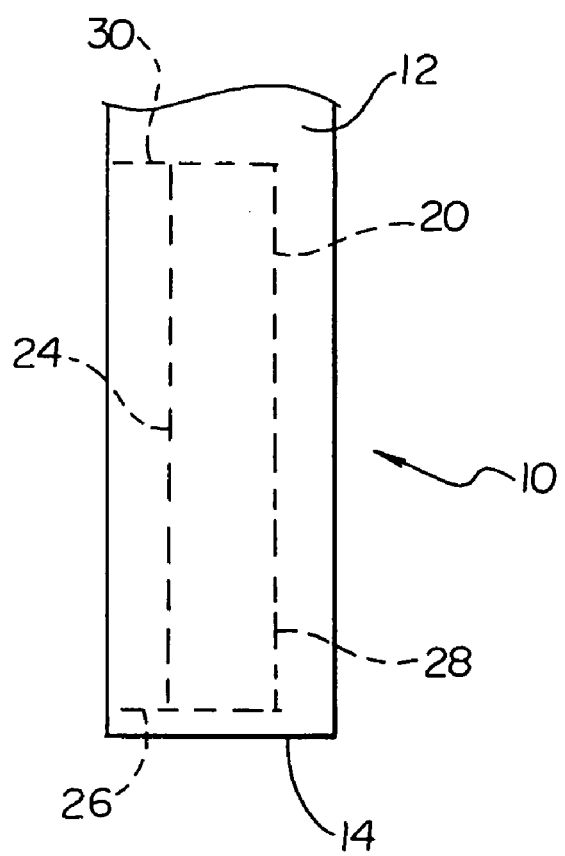
FIG. 3G is a top plan view of an embodiment of an inventive medical device having a rotational marker at a fourth rotational orientation.
Figure 3H:
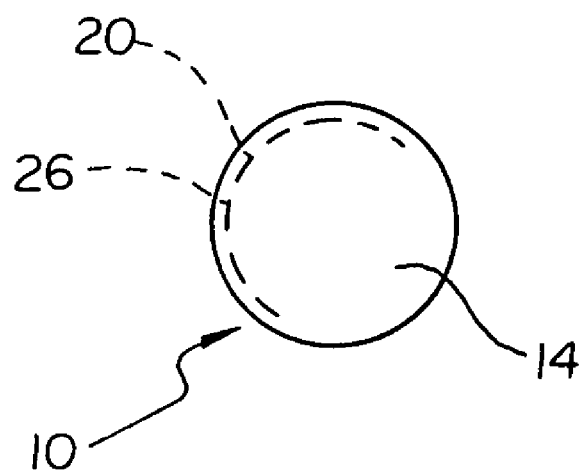
FIG. 3H is an end view of an embodiment of an inventive medical device having a rotational marker at a fourth rotational orientation.

FIGS. 3A, 3C, 3E and 3G depict top plan views of a medical device 10 having a rotational marker 20. FIGS. 3B, 3D, 3F and 3H depict end views of a medical device 10 having a rotational marker 20. FIGS. 3C and 3D depict the medical device 10 in a position rotated 90° from the position depicted in FIGS. 3A and 3B, respectively. As shown in FIG. 3C, when a first portion 24 of a rotational marker 20 is directly beneath a third portion 28, the portions will appear as a single line in plan view. FIGS. 3E-3H depict the medical device 10 in rotational positions intermediate to the positions shown in FIGS. 3A and 3B and FIGS. 3C and 3D. FIGS. 3A-3H show how the rotational orientation of a medical device 10 may be determined by viewing a rotational marker 20 through an imaging device after the medical device 10 has been inserted into a bodily lumen. When a graft portion 42 of an implantable medical device 40 is arranged in relation to the rotational marker 20, exact placement of the graft portion 42 within a bodily lumen is facilitated.

Figure 4:
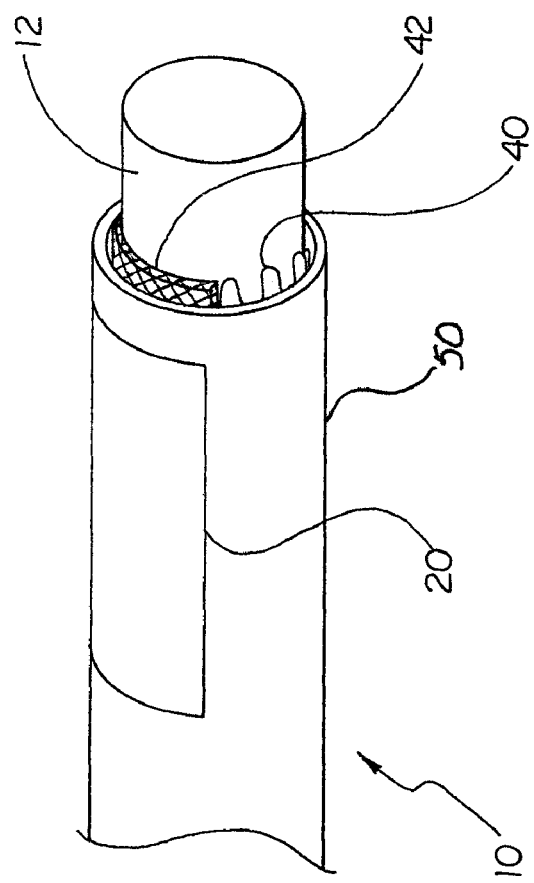
FIG. 4 is a perspective view of another embodiment of an inventive medical device having a rotational marker.

FIG. 4 shows a medical device 10 comprising a catheter shaft 12 and a catheter outer wall or sheath 50. An implantable medical device 40 having a graft portion 42 is mounted upon a catheter shaft 12 beneath the sheath 50. The implantable medical device 40 may comprise a self-expanding stent. Thus, in some embodiments, the sheath 50 may constrain the implantable medical device 40. As the sheath 50 is retracted, the implantable medical device 40 is allowed to expand. A lubricious coating between the sheath 50 and the implantable medical device 40 may be desirable.

The sheath 50 may include a rotational marker 20. Desirably, the sheath 50 is positioned such that the rotational marker 20 overlays the graft portion 42 or otherwise indicates the rotational location of the graft portion. The rotational marker 20 may also indicate the approximate length of the implantable medical device 40.

In some embodiments wherein a sheath 50 includes a rotational marker 20, it may be desirable to provide an axial coupling between the sheath 50 and the catheter shaft 12 or between the sheath 50 and the implantable medical device 40 to prevent rotation. An axial coupling desirably prevents rotation between the components that are axially coupled to one another. Thus, a rotational marker 20 may be rotationally fixed in place above a graft portion 42, and will remain directly above the graft 42 until the sheath 50 is displaced axially, such as by retraction.

Figure 5:
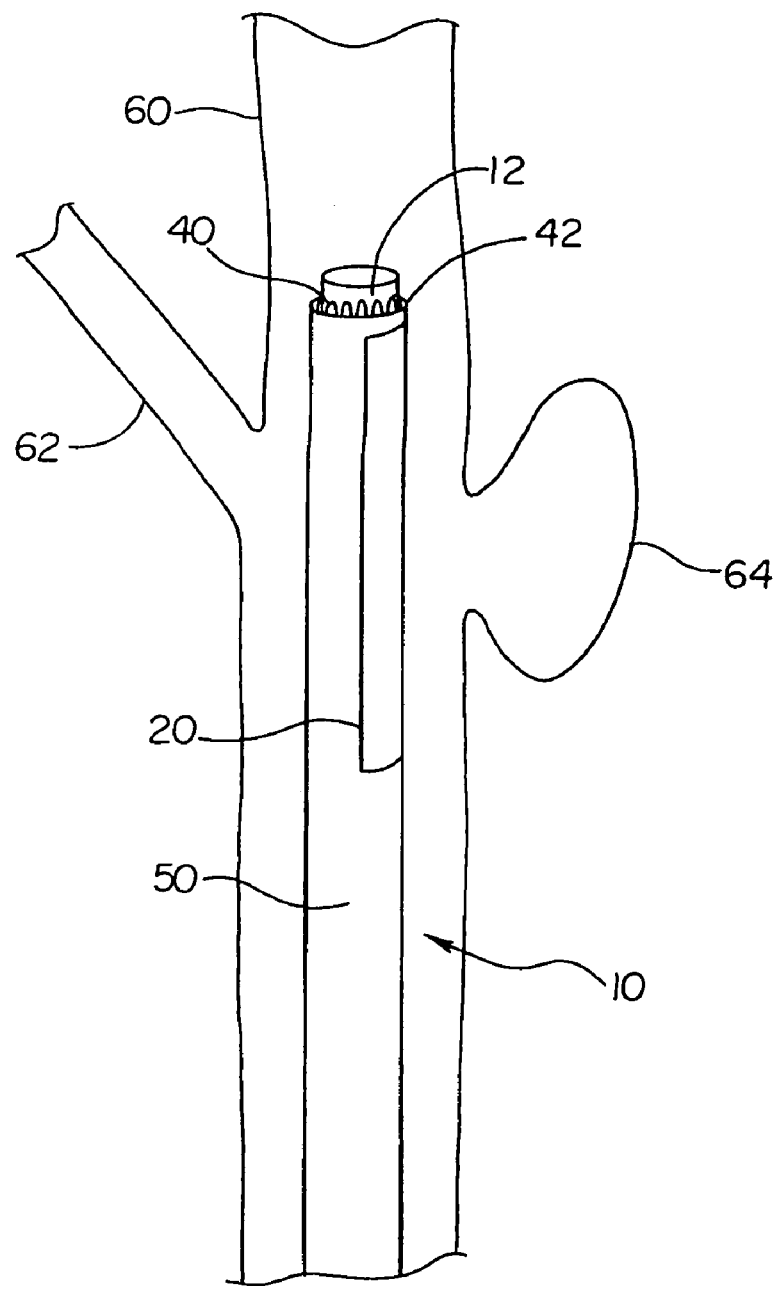
FIG. 5 is a view of an embodiment of an inventive medical device having a rotational marker positioned within a bodily lumen.

FIG. 5 depicts an implantable medical device 40 being delivered for placement within a bodily lumen 60 having a sidebranch 62 and an aneurysm 64. In this embodiment, the medical device 10 comprises a catheter shaft 12, a sheath 50 and a rotational marker 20. An implantable medical device 40 having a graft portion 42 is arranged between the catheter shaft 12 and the sheath 50. The rotational marker 20 is positioned to indicate the approximate location and rotational orientation of the graft portion 42. Thus, the rotational marker 20 facilitates placement of the implantable medical device 40 such that the graft portion 42 can cover the aneurysm 64 without a consequential blockage of the sidebranch 62.

Figure 6:
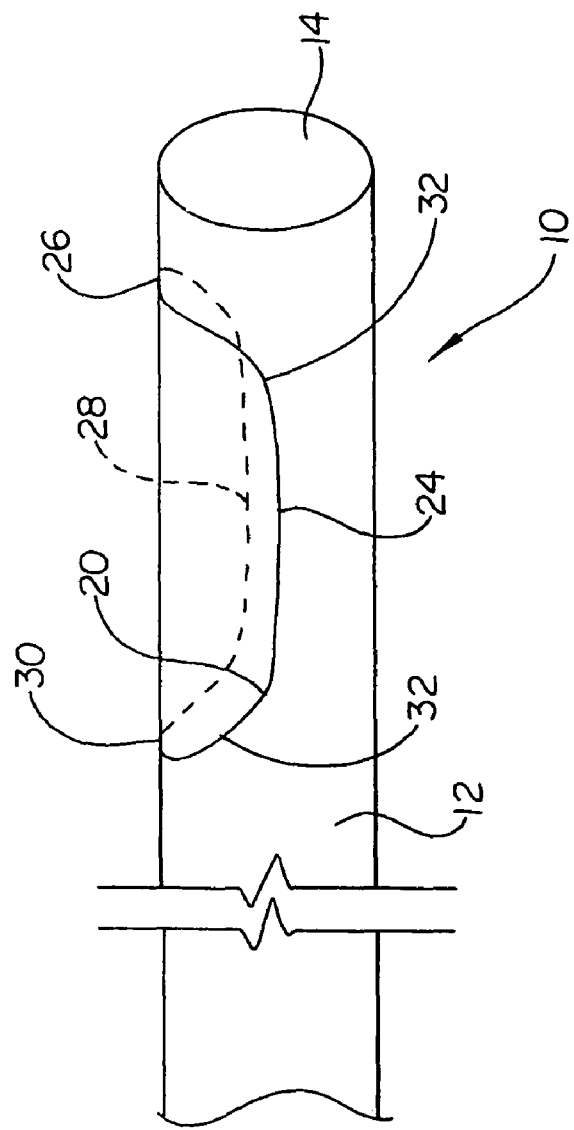
FIG. 6 is a perspective view of another embodiment of an inventive medical device having a rotational marker.

In another embodiment, a rotational marker 20 comprising a wire may traverse a generally sinuous or serpentine path, as shown in FIG. 6. A serpentine wire marker 20 may include sections that are generally lengthwise 24, 28 and sections that are generally circumferential 26, 30. Generally lengthwise sections 24, 28 may be substantially parallel to the longitudinal axis of the device 10. A serpentine wire marker 20 may further include intermediate sections 32 that are neither circumferential nor parallel to the longitudinal axis of the device 10.

The path of a serpentine wire marker 20 may be arranged to generally indicate the edges of a graft portion 42 of an implantable medical device 40. A serpentine wire marker 20 will desirably indicate the rotational position of a graft portion 42 under fluoroscopy or MRI.

Figure 7:
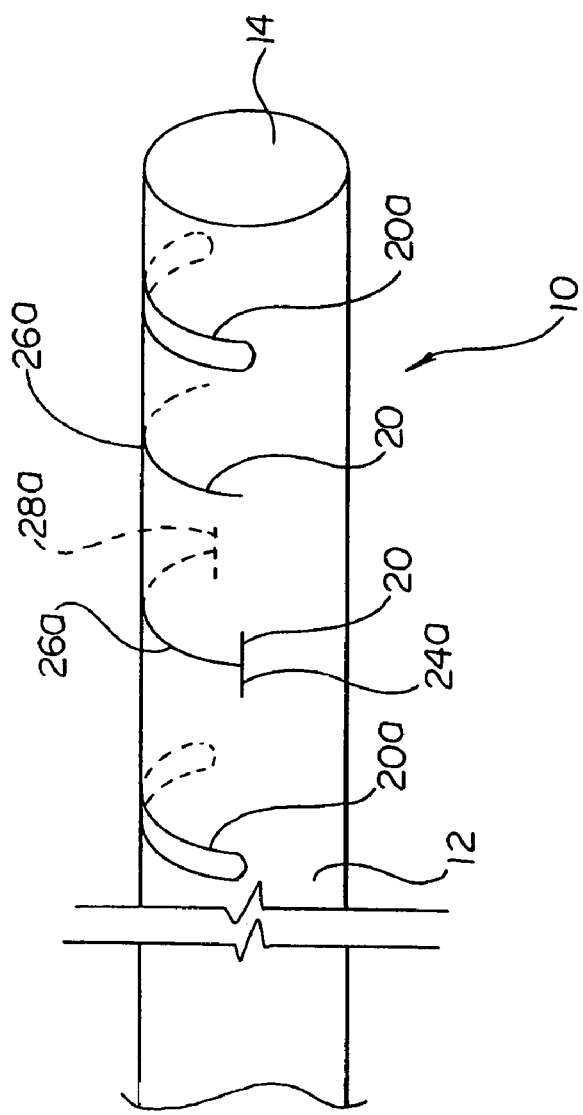
FIG. 7 is a perspective view of an inventive medical device having further embodiments of rotational markers.

FIG. 7 depicts additional embodiments of rotational markers 20. A marker 20 may comprise a generally circumferential length of wire 26a, which may have any span desired. A marker may further comprise at first lengthwise portion 24a and a second lengthwise portion 28a. A marker 20 may comprise a generally serpentine closed loop 20a spanning a substantially shorter length of the medical device 10 than the length of an eventual implantable medical device 40.

Figure 8:
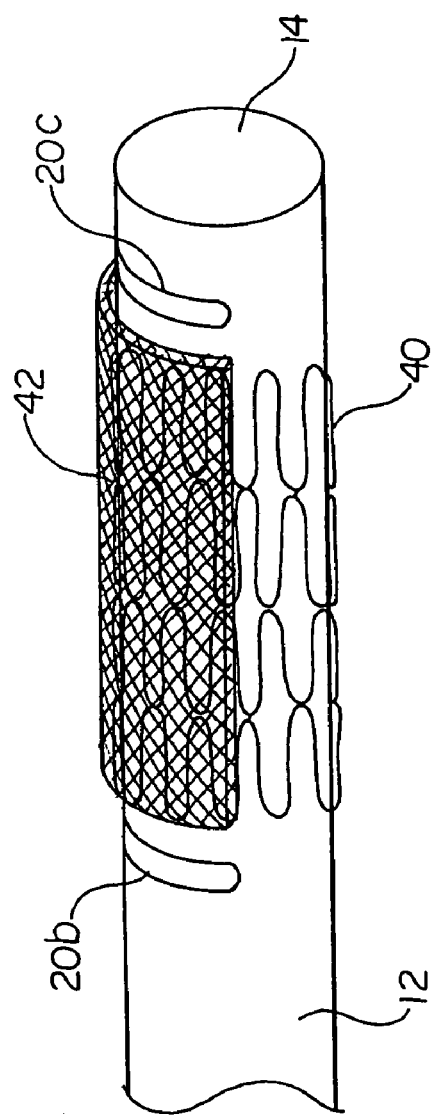
FIG. 8 is a perspective view of another embodiment of an inventive medical device having a rotational marker.

An inventive medical device 10 may include a plurality of rotational markers 20. The markers 20 may be placed to collectively indicate the position of an eventual implantable medical device 40 or graft portion 42. For example, as shown in FIG. 8, a first rotational marker 20b may be mounted near a proximal end of a graft portion 42, and a second rotational marker 20c may be mounted near a distal end of a graft portion 42. Thus, rotational markers 20 may comprise proximal markers 20b and distal markers 20c.

Figure 9:
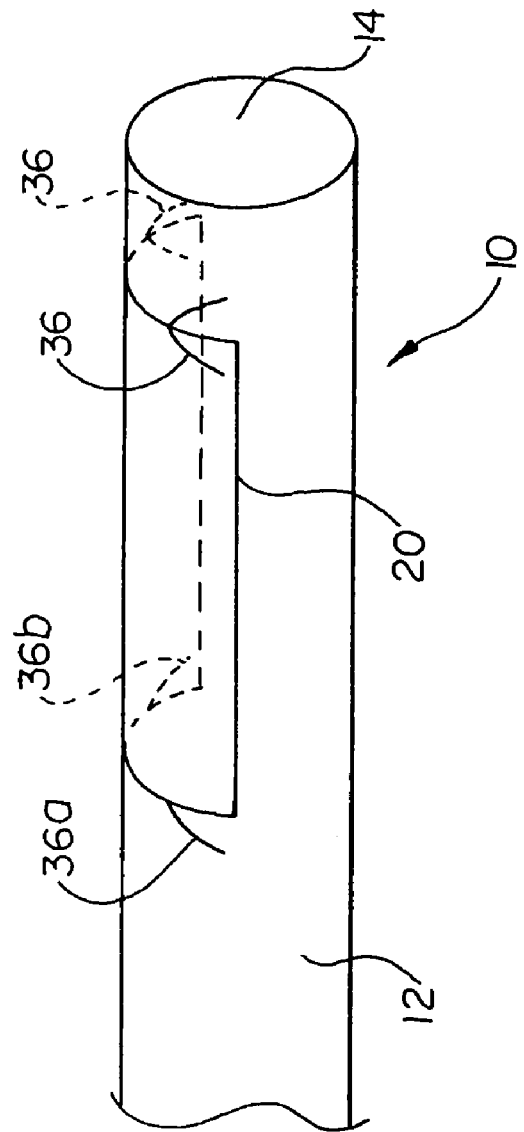
FIG. 9 is a perspective view of another embodiment of an inventive medical device having a rotational marker.
Figure 10:
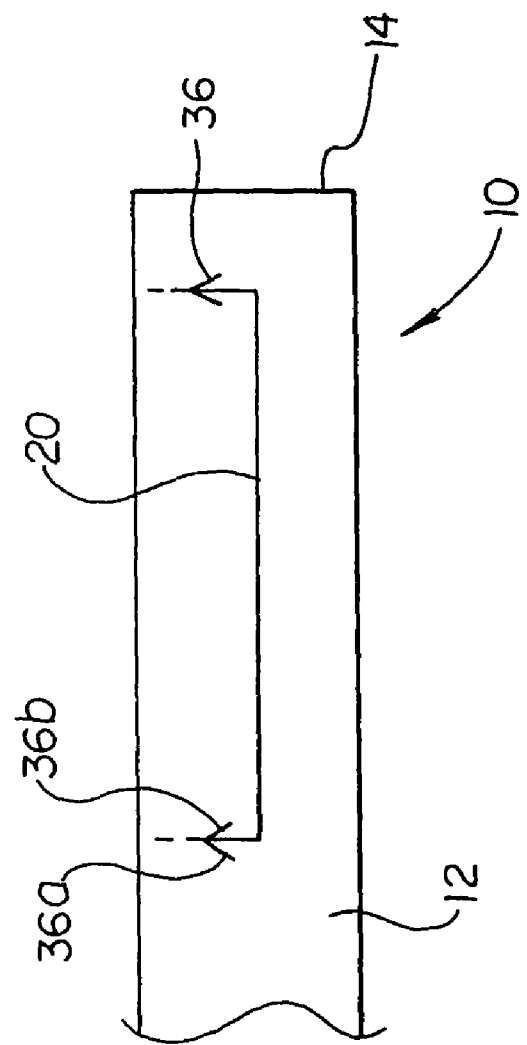
FIG. 10 is a plan view of the medical device according to FIG. 9.

FIGS. 9 and 10 show further embodiments of a medical device 10 having a rotational marker 20. A rotational marker 20 may further comprise directional indicators 36. Directional indicators 36 may be positioned to further indicate the position of an implantable medical device 40 or graft portion 42 when the marker 20 is viewed through an imaging system. Directional indicators 36 may be made from the same materials as the rest of the marker 20, or may comprise a different material to result in greater or lesser visibility than other portions of the marker 20 when viewed through an imaging system.

In one embodiment, as shown in FIG. 10, directional indicators 36 of a rotational marker 20 may appear as two-dimensional symbols in plan view, such as arrows. Thus, the directional indicators 36 may be positioned to indicate the direction of a graft portion 42. Directional indicators 36 may be arranged to form a recognizable symbol upon an imaging device throughout only a predetermined rotational range, such as 10° to 30°.

Further, a directional indicator 36 may comprise only a portion of a symbol that will be viewable through an imaging device. Thus, a directional indicator 36 and another part of the marker 20 can form a symbol. In some embodiments, two separate directional indicators 36a, 36b can form a symbol. FIG. 9 shows a first directional indicator 36a and a second directional indicator 36b. When the rotational marker 20 is viewed as a two-dimensional image as shown in FIG. 10, for example by fluoroscopy, the first and second indicators 36a, 36b may combine to depict a complete arrow over a narrow range of rotation of the medical device 10, such as 10° or less in some embodiments, and 5° or less in some embodiments.

Figure 11:
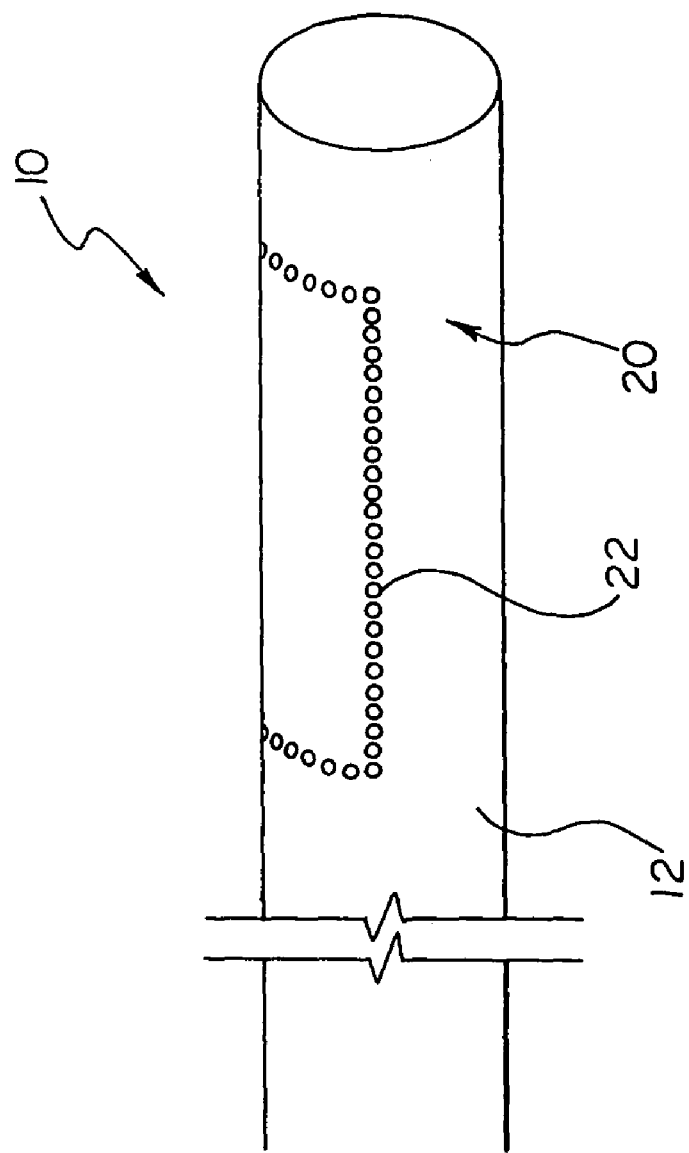
FIG. 11 is a perspective view of an embodiment of an inventive medical device having a rotational marker system.

Referring to FIG. 11, in some embodiments, a plurality of individual markers 22 may collectively comprise a rotational marker 20 or a rotational marker 20 system. Individual markers 22 may be attached to the device 10 using any suitable method. Individual markers 22 may follow any suitable pattern, and may form a straight, arcuate, sinuous or serpentine path. Individual markers 22 may be positioned to form a symbol when viewed upon an imaging device at a correct rotational orientation.

Figure 12:
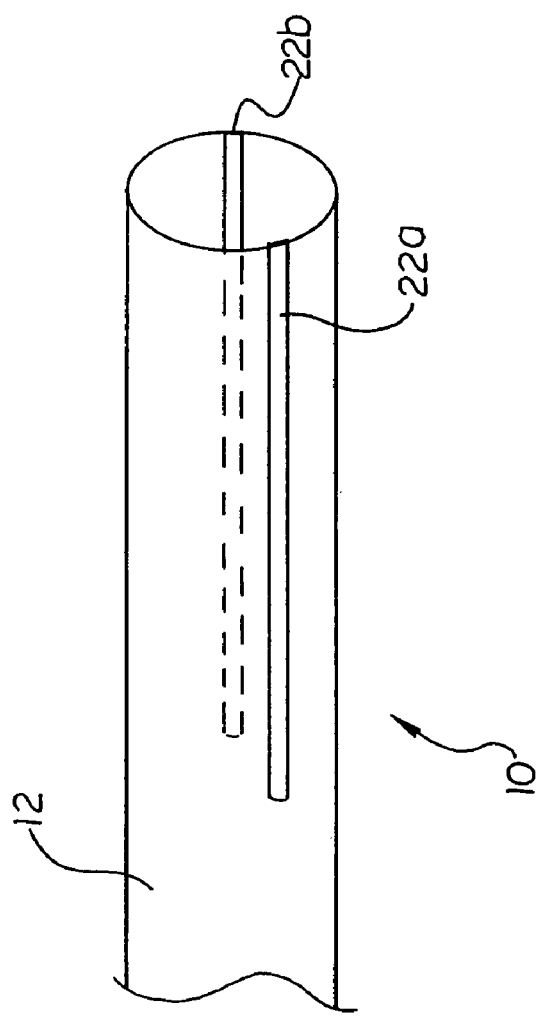
FIG. 12 is a perspective view of another embodiment of an inventive medical device having a rotational marker system.
Figure 13:
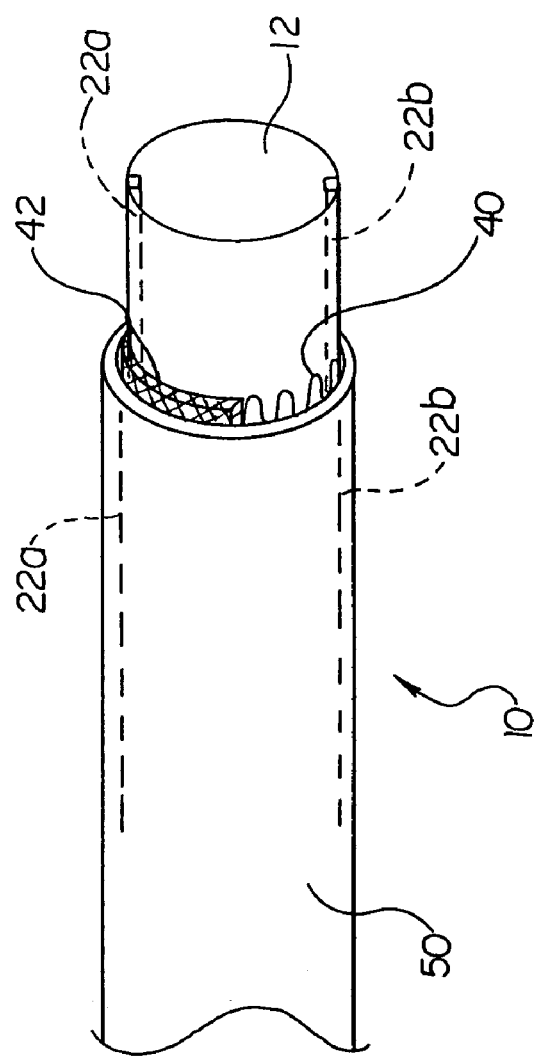
FIG. 13 is a perspective view of another embodiment of an inventive medical device having a rotational marker system.

FIGS. 12 and 13 depict further embodiments of a medical device 10 having a rotational marker system comprising a first individual marker 22a and a second individual marker 22b. Desirably, the first individual marker 22a will appear to have a greater luminosity than the second individual marker 22b when viewed upon an imaging device. Thus, the first individual marker 22a may be more visible than the second individual marker 22b. In one embodiment the first individual marker 22a comprises a different material than the second individual marker 22b. In another embodiment, the first individual marker 22b may comprise the same material as the second individual marker 22a but have a greater mass.

In some embodiments, an inventive medical device 10 may include a first individual marker 22a and a second individual marker 22b, each individual marker 22a, 22b having an enhanced radiopacity when compared to other portions of the device 10. Desirably, the first individual marker 22a may have a higher degree of radiopacity than the second individual marker 22b.

FIG. 13 shows a medical device 10 comprising a catheter having a catheter shaft 12 and a sheath 50. An implantable medical device 40 having a graft portion 42 is mounted upon the catheter shaft 12. The catheter shaft 12 may include a first individual marker 22a and a second individual marker 22b. The sheath 50 may include a first individual marker 22a and a second individual marker 22b.

A first individual marker 22a and a second individual marker 22b may be placed anywhere upon the medical device 10 to allow an operator to determine the rotational orientation of the device 10. In one embodiment, the individual markers 22a, 22b may comprise lengthwise strips or wires. The length and placement of markers 22 comprising strips may be chosen to represent the bounds of an implantable medical device 40. For example, the length of a strip marker 22 may be equal to the length of a stent 40.

In some embodiments, a first individual marker 22a and a second individual marker 22b may be placed near the opposing longitudinal ends of a graft portion 42 of a stent 40. Thus, the bounds of the graft 42 may be visualized upon an imaging device.

In some embodiments, as shown in FIG. 13, a first individual marker 22a may be placed to correspond to the midpoint of a graft portion 42 about the circumference of the implantable medical device 40. A second individual marker 22b may be placed to correspond to the middle of the ungrafted portion of a stent 40. In some embodiments, the first individual marker 22a may be 180° away from the second individual marker 22b, or placed directly across the implantable medical device 40.

Figure 14:
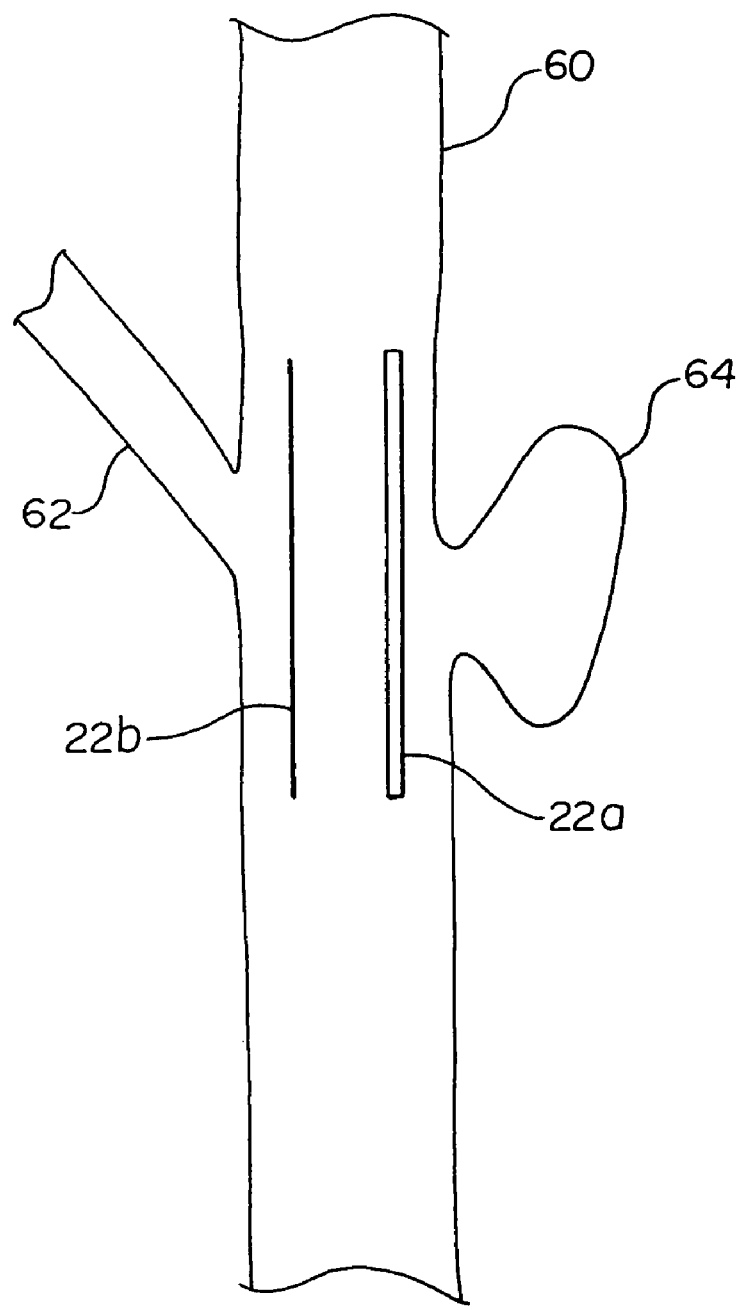
FIG. 14 is a view of an embodiment of an inventive medical device having a rotational marker positioned within a bodily lumen.

FIG. 14 depicts an image of a rotational marker 20 system comprising a first individual marker 22a and a second individual marker 22b as viewed upon an imaging device within a bodily lumen 60. The first individual marker 22a desirably appears brighter, more intense or more visible than the second individual marker 22b, and may be used to determine the rotational orientation of a graft portion 42 for proper placement over an aneurysm 64.

In some embodiments, an inventive medical device 10 may comprise an implantable medical device 40 having a rotational marker 20. When a rotational marker 20 is included on an implantable medical device 40, rotational markers are not required on a delivery system. Rotational markers 20 may be attached to an implantable medical device 40 using any suitable method, such as by adhesive or by the application RF energy, IR energy, UV energy, laser energy, ultra-sonic energy, electrical energy, and any combination thereof. Further, markers 20 may be contained within a graft portion 42, such as being sandwiched between layers of a graft 42 and methods disclosed in U.S. patent application Ser. No. 10/600, 022, incorporated herein by reference.

Figure 15:
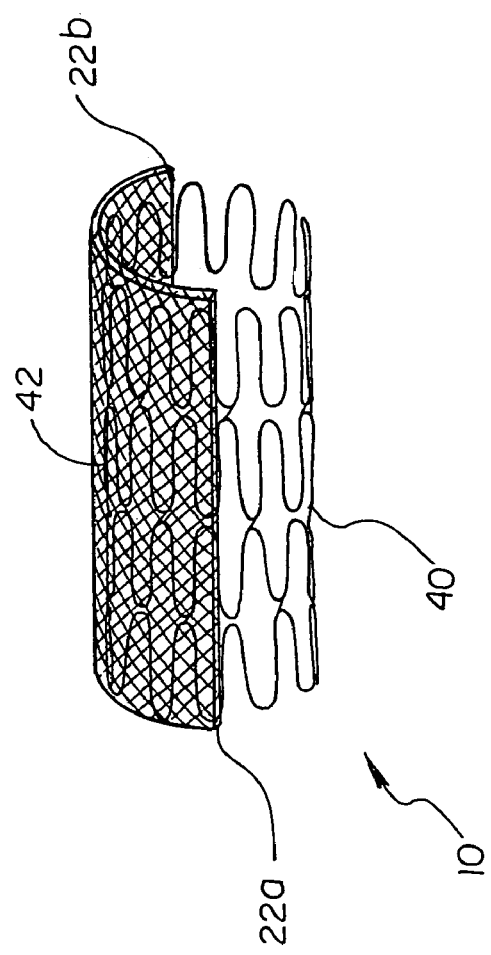
FIG. 15 is a perspective view of another embodiment of an inventive medical device having a rotational marker system.

FIG. 15 shows a medical device 10 comprising an implantable medical device 40 having a first individual marker 22a and a second individual marker 22b. The individual markers 22a, 22b are shown near the edges of a graft portion 42. In other embodiments, a first individual marker 22a may be placed to correspond to the midpoint of a graft portion 42 about the circumference of the implantable medical device 40. A second individual marker 22b may be placed to correspond to the middle of the ungrafted portion of a stent 40. In some embodiments, the first individual marker 22a may be 180° away from the second individual marker 22b, or placed directly across the implantable medical device 40.

Figure 16:
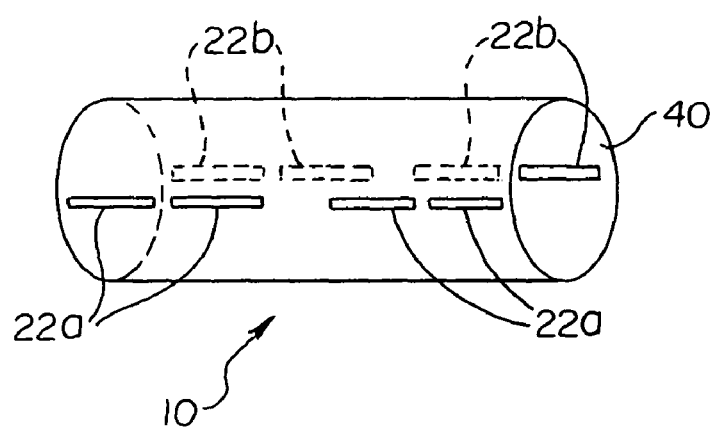
FIG. 16 is a perspective view of another embodiment of an inventive medical device having a rotational marker system.

FIG. 16 shows a medical device 10 comprising an implantable medical device 40 having a plurality of first individual markers 22a and a plurality of second individual markers 22b. Individual markers 22a, 22b in this embodiment do not span the entire length of the implantable medical device 40. Shorter markers 22a, 22b allow for a shift in positioning of the markers as may be required during expansion of the implantable medical device 40.

Figure 17:
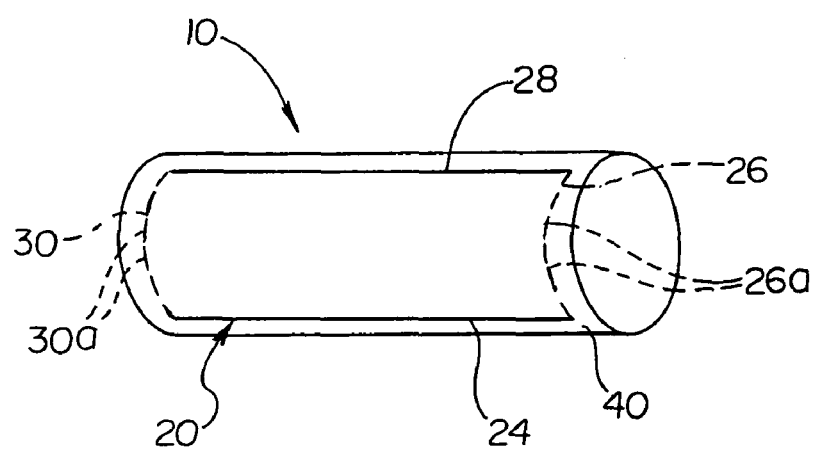
FIG. 17 is a perspective view of another embodiment of an inventive medical device having a rotational marker system.
Figure 18:
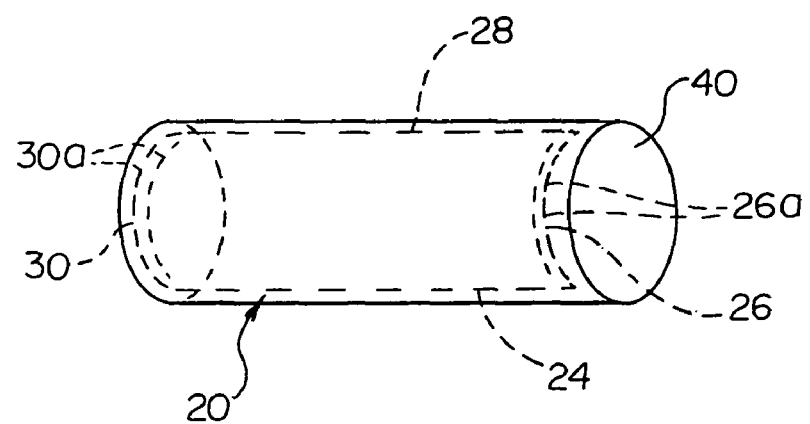
FIG. 18 is a perspective view of another embodiment of an inventive medical device having a rotational marker system.

FIGS. 17 and 18 show a medical device 10 comprising an implantable medical device 40 having a rotational marker 20. The rotational marker may comprise a first portion 24 extending along the length of the medical device 10, and a second portion 26 extending about a radial arc or circumferential portion of the implantable medical device 40. The marker 20 may further include a third portion 28 extending along the length of the medical device 10, and a fourth portion 30 extending about a radial arc or circumferential portion of the implantable medical device 40.

In some embodiments, the arcuate portions 26, 30 of a rotational marker 20 may comprise a plurality of arcuate elements 26a, 30a. Arcuate elements 26a, 30a may be arranged in a generally linear, single file path, or may have overlapping portions as shown in FIG. 18. Overlapping portions may allow the arcuate sections 26, 30 to be more visible when viewed through an imaging device. Further, as an implantable medical device 40 expands, arcuate elements 26a, 30a may displace with respect to one another as the diameter of the implantable medical device 40 grows. Thus, an arcuate section 26, 30 comprising arcuate elements 26a, 30a will allow for expansion of an implantable medical device 40.

Figure 19:
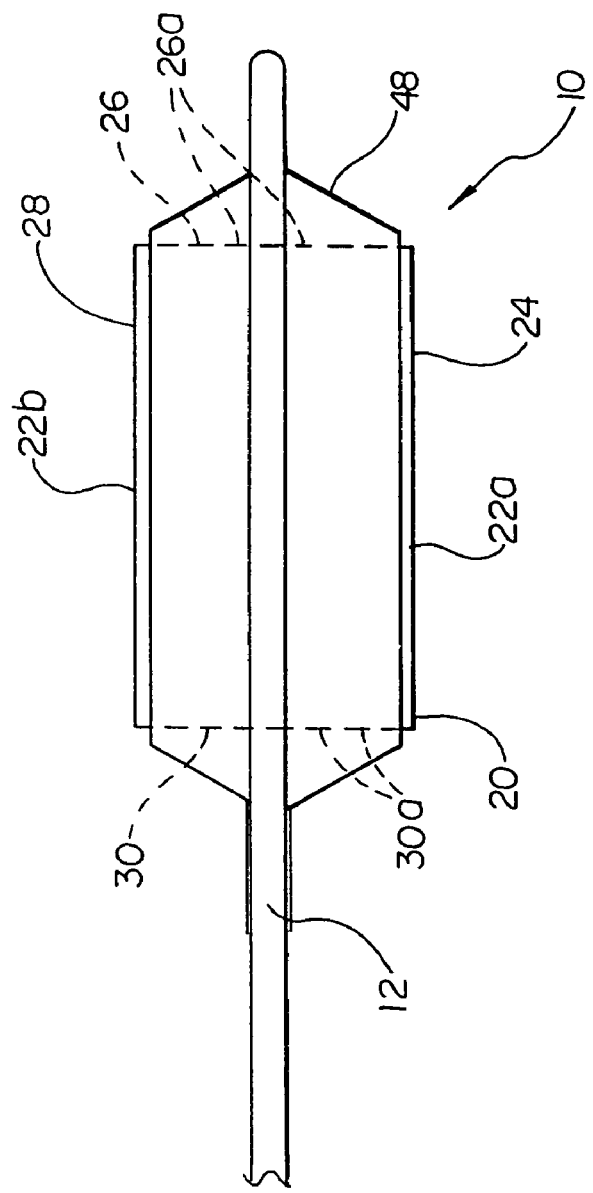
FIG. 19 is a perspective view of another embodiment of an inventive medical device having a rotational marker system.

In other embodiments, a medical device 10 may comprise a balloon catheter having a rotational marker 20, as shown in FIG. 19. A rotational marker 20 may be attached directly to an expansion balloon 48 using any of the methods disclosed herein.

In one embodiment, a balloon 48 may have a rotational marker 20 comprising a first individual marker 22a and a second individual marker 22b. Desirably, the first individual marker 22a will appear to have a greater luminosity than the second individual marker 22b when viewed upon an imaging device.

In another embodiment, a balloon 48 may have a rotational marker 20 comprising a first portion 24 extending along the length of the balloon 48, and a second portion 26 extending about a radial arc or circumferential portion of the balloon 48. The marker 20 may further include a third portion 28 extending along the length of the balloon 48, and a fourth portion 30 extending about a radial arc or circumferential portion of the balloon 48. Lengthwise sections 24, 28 may comprise a plurality of portions or elements. Similarly, arcuate sections 26, 30 may comprise a plurality of arcuate elements 26a, 30a.

Figure 20:
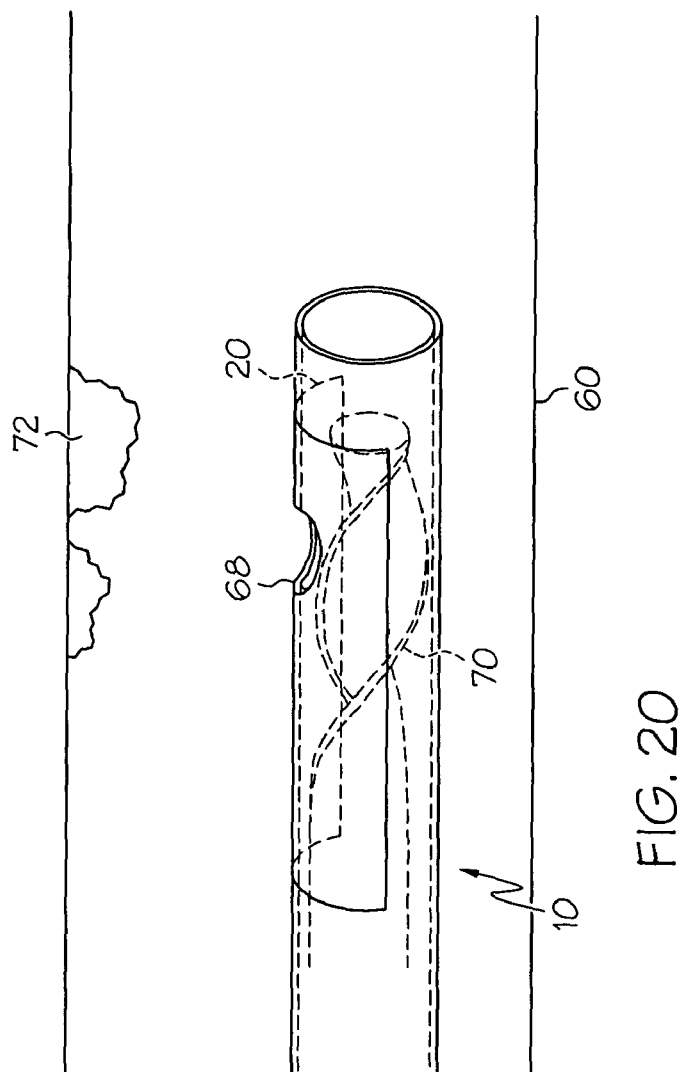
FIG. 20 is a perspective view of another embodiment of an inventive medical device having a rotational marker system disposed within a bodily lumen.

Referring to FIG. 20, in another embodiment, a medical device 10 may include a rotational marker 20, or a rotational marker system. The device may comprise a circumferential wall having a lumen 52 extending therethrough. A wall of the medical device 10 may further include an aperture or port 68. Desirably, the port 68 may be positioned such that orientation and placement of the port 68 may be determined via the image of a rotational marker 20 upon an imaging device. It is also within the scope of the invention for port 68 to be provided with a radiopaque marker on the rim of the port. The radiopaque marker may be of any suitable type including, but not limited to a coating.

The medical device 10 may further include a rotational ablation device 70, and the medical device 10 may be used to remove plaque and other deposits 72 from a vessel wall as disclosed in U.S. Pat. No. 6,179,851, the entire disclosure of which is incorporated herein by reference.

The invention is also directed to a method of using an inventive medical device in an atherectomy procedure. The medical device 10 may be inserted into a bodily lumen 60 and maneuvered to a vessel location having a deposit 72, such as plaque, a clot or another type of thrombus. An imaging device may be used to view a rotational marker 20 to facilitate positioning the device 10 with the port 68 immediately adjacent to a deposit 72. As the device 10 is moved in the direction of the deposit 72, rotational ablation device 70 may remove portions of the deposit 72 from the vessel wall. The portions that have been removed may then enter the port 68. Desirably, the removed deposit 72 material may be carried away within a lumen 52 of the medical device 10.

Further embodiments of rotational ablation devices may be incorporated into or used in conjunction with an inventive medical device 10, such as disclosed in U.S. Pat. Nos. 6,596,005, 6,503,261 and 6,270,509, the entire disclosures of which are incorporated herein by reference.

Any of the inventive embodiments of rotational markers and/or rotational marker systems may be used with a rotational ablation device or a medical device that includes or may work in conjunction with a rotational ablation device.

The invention is also directed to a method of using any of the inventive devices disclosed herein for determining the rotational orientation of a device within a bodily lumen. For example, a method of using an embodiment of the inventive medical device 10 for properly positioning a graft portion 42 generally comprises delivering the medical device 10 to a deployment location within a bodily lumen 60, as shown in FIGS. 5 and 14. In some embodiments, the medical device 10 may comprise a catheter 12 or introducer. In some embodiments, the medical device 10 may comprise an implantable medical device 40, and may be delivered to the deployment site with an introducer, such as a prior art catheter or an inventive catheter 12. The deployment location and the marker 20 may be viewed upon an imaging device. The rotational orientation of the medical device 10, and consequentially the rotational orientation of the graft portion 42, may be determined by the image of the rotational marker 20 appearing upon the imaging device. If the marker 20 includes portions that indicate the length of an implantable medical device 40, the axial location of the implantable medical device 40 may also be determined in relative to the deployment site.

Rotation of the proximal end of the introducer will cause a rotation of the medical device 10 and of the rotational marker 20 and graft portion 42. The rotational marker 20 and graft portion 42 may then be properly positioned rotationally with respect to an aneurysm 64. Deployment of an implantable medical device 40 may be accomplished by any known method, such as by expansion balloon 48 or by retraction of a sheath 50 and self-expansion of the implantable medical device 40.

Any of the inventive medical devices 10 disclosed herein may be provided with a uniform diameter or may taper in portions or along the entire length of the device. Further, the width and/or thickness of the various portions of a device may increase or decrease along a given portion of the device.

The inventive devices 10 may also be provided with various bio-compatible coatings. For example, the inventive devices may be provided with lubricious coatings. The inventive devices may also be provided with drug-containing coatings which release drugs over time. The inventive devices may also be provided with a sugar or more generally a carbohydrate and/or a gelatin to maintain a stent on a catheter or balloon during delivery of the stent to a desired bodily location.

A coating may comprise one or more non-genetic therapeutic agents, genetic materials and cells and combinations thereof as well as other polymeric coatings.

Non-genetic therapeutic agents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, anti-thrombin anticodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

Genetic materials include anti-sense DNA and RNA, DNA coding for, anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor αand β, platelet-derived endothelial growth factor, platelet-derived growth factor, tumor necrosis factor α, hepatocyte growth factor and insulin like growth factor, cell cycle inhibitors including CD inhibitors, thymidine kinase ("TK") and other agents useful for interfering with cell proliferation the family of bone morphogenic proteins ("BMP"s"), BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Desirable BMP"s are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA"s encoding them.

Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (for example, BAYHDROL®), fibrin, collagen and derivatives thereof, polysaccharides such as celluloses, starches, dextrans, alginates and derivatives, hyaluronic acid, squalene emulsions. Polyacrylic acid, available as HYDROPLUS® (Boston Scientific Corporation, Natick, Mass.), and described in U.S. Pat. No. 5,091,205, the disclosure of which is hereby incorporated herein by reference, is particularly desirable. Even more desirable is a copolymer of polylactic acid and polycaprolactone.

The inventive devices may find use in coronary arteries, renal arteries, peripheral arteries including iliac arteries, arteries of the neck and cerebral arteries, as well as other body structures, including but not limited to arteries, veins, biliary ducts, urethras, fallopian tubes, bronchial tubes, the trachea, the esophagus, the prostate and the bowels.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. An apparatus, comprising:
a medical device and a marker wire coupled to said medical device, the medical device having a length and a longitudinal axis, the marker wire comprising four contiguous portions defining the perimeter of a closed area, wherein two portions extend in a circumferential direction about the longitudinal axis of the medical device but not entirely about the circumference of the medical device, and two portions linearly extend in a direction parallel to the longitudinal axis of the medical device, the closed area having a length that is less than the length of the medical device, wherein the rotational orientation of the marker wire may be determined using an imaging device when the medical device is positioned within a bodily lumen;
a first directional indicator coupled to said medical device and intersecting said marker wire, the first directional indicator comprising a first portion of a symbol;
a second directional indicator coupled to said medical device and intersecting said marker wire, said second directional indicator offset from said first directional indicator, the second directional indicator comprising a second portion of the symbol;
wherein images of said first and second directional indicators physically connect to form the symbol when viewed from a proper rotational orientation about the longitudinal axis when viewed orthogonally to the longitudinal axis using an imaging device.

2. The apparatus of claim 1, wherein the marker wire is continuous.

3. The apparatus of claim 1, wherein the marker wire comprises a closed circuit.

4. The apparatus of claim 1, wherein the medical device comprises a catheter.

5. The apparatus of claim 1, wherein the medical device comprises a catheter sheath.

6. The apparatus of claim 1, wherein the medical device comprises a device that may be implanted within a bodily lumen.

7. The apparatus of claim 1, wherein the medical device comprises a stent.

8. The apparatus of claim 7, wherein the stent is self expanding.

9. The apparatus of claim 7, wherein the stent further comprises a graft that covers a portion of the stent, wherein the graft is aligned with the closed area defined by the marker wire.

10. The apparatus of claim 9, wherein the graft defines an arc length, and the first portion of the marker wire defines a similar arc length.

11. The apparatus of claim 1, wherein the medical device comprises an expansion balloon.

12. The apparatus of claim 1, wherein the marker wire comprises an MRI marker.

13. The apparatus of claim 1, further comprising a lumen and a port.

14. The apparatus of claim 13, wherein the lumen is arranged to carry away bodily material.

15. The apparatus of claim 13, wherein said marker wire extends about a rim of the port.

16. The apparatus of claim 1, further comprising a rotational ablation device.

17. An apparatus, comprising:
a medical device and a marker wire coupled to said medical device, the medical device having a longitudinal axis, the marker wire comprising four contiguous portions defining the perimeter of a closed area, wherein two portions extend in a circumferential direction about the longitudinal axis of the medical device but not entirely about the circumference of the medical device, and two portions linearly extend in a direction parallel to the longitudinal axis of the medical device, wherein the rotational orientation of the marker wire may be determined using an imaging device when the medical device is positioned within a bodily lumen;
a first directional indicator coupled to said medical device and oriented in a direction non-parallel to the longitudinal axis, the first directional indicator intersecting said marker wire and comprising a first portion of a symbol;
a second directional indicator coupled to said medical device offset from said first directional indicator and oriented in a direction non-parallel to the longitudinal axis, the second directional indicator intersecting said marker wire and comprising a second portion of the symbol;

wherein images of said first and second directional indicators physically connect to form the symbol when viewed from a proper rotational orientation about the longitudinal axis when viewed orthogonally to the longitudinal axis using an imaging device.

18. The apparatus of claim 17, wherein the symbol is an arrow.

19. The apparatus of claim 17, wherein the symbol is viewable over a rotational range of 30° or less.

20. The apparatus of claim 17, wherein the second directional indicator is offset from the first directional indicator in a circumferential direction.

21. The apparatus of claim 20, wherein the symbol is an arrow.

22. The apparatus of claim 20, further comprising a partial graft, wherein the symbol indicates the orientation of the partial graft.

23. The apparatus of claim 20, wherein the symbol is viewable over a rotational range of 5° or less.

24. A method of positioning an implantable medical device within a bodily lumen, comprising:

a) providing a medical device having a longitudinal axis and a rotational marker coupled to the medical device, the rotational marker comprising:

a marker wire comprising four contiguous portions defining the perimeter of a closed area, wherein two portions extend in a circumferential direction about the longitudinal axis of the medical device but not entirely about the circumference of the medical device, and two portions linearly extend in a direction parallel to the longitudinal axis of the medical device the closed area having a length that is less than the length of the medical device, wherein the rotational orientation of the marker wire may be determined using an imaging device when the medical device is positioned within a bodily lumen, and a first directional indicator coupled to said medical device, the first directional indicator intersecting said marker wire and comprising a first portion of a symbol, a second directional indicator coupled to said medical device offset from said first directional indicator, the second directional indicator intersecting said marker wire and comprising a second portion of the symbol, wherein images of said first and second directional indicators physically connect to form the symbol when viewed from a proper rotational orientation using an imaging device;

b) inserting the medical device into a bodily lumen and maneuvering the device to a worksite;

c) viewing the worksite and the device through an imaging device, the rotational marker and the first and second directional indicators being visible upon the imaging device, wherein the rotational orientation of the marker wire may be determined using the imaging device;

d) positioning the medical device to a proper rotational orientation using the rotational marker and the first and second directional indicators as viewed orthogonally to the longitudinal axis upon the imaging system.

\* \* \* \* \*